(12) United States Patent
Anderson et al.

(10) Patent No.: US 6,466,323 B1
(45) Date of Patent: Oct. 15, 2002

(54) SURFACE PLASMON RESONANCE SPECTROSCOPY SENSOR AND METHODS FOR USING SAME

(75) Inventors: Brian Benjamin Anderson, N. Augusta, SC (US); Stanley Eugene Nave, Evans, GA (US)

(73) Assignee: Westinghouse Savannah River Company, L.L.C., Aiken, SC (US)

( * ) Notice: Subject to any disclaimer, the term of this patent is extended or adjusted under 35 U.S.C. 154(b) by 0 days.

(21) Appl. No.: 09/447,155

(22) Filed: Nov. 23, 1999

(51) Int. Cl.[7] ............................................. G01N 21/55
(52) U.S. Cl. ...................................................... 356/445
(58) Field of Search ................................ 356/445, 300, 356/301; 600/310, 314–318, 322, 323

(56) References Cited

U.S. PATENT DOCUMENTS

| | | | |
|---|---|---|---|
| 4,076,420 A | 2/1978 | De Maeyer et al. | 356/73 |
| 4,802,761 A | 2/1989 | Bowen et al. | 356/301 |
| 4,834,494 A | 5/1989 | DeMeritt et al. | 350/96.21 |
| 4,948,214 A | 8/1990 | Hamblen | 350/413 |
| 4,997,278 A | 3/1991 | Finlan et al. | 356/128 |
| 5,332,690 A | 7/1994 | Cho et al. | 437/126 |
| 5,416,624 A | 5/1995 | Karstensen | 359/114 |
| 5,485,277 A | 1/1996 | Foster | 356/445 |
| 5,502,560 A | 3/1996 | Anderson et al. | 356/128 |
| 5,610,708 A | 3/1997 | Anderson et al. | 356/128 |
| 5,724,151 A | 3/1998 | Ryley et al. | 356/432 |
| 5,729,641 A | 3/1998 | Chandonnet et al. | 385/2 |
| 5,835,645 A | 11/1998 | Jorgenson et al. | 385/12 |
| 5,858,799 A | 1/1999 | Yee et al. | 436/164 |
| 5,864,397 A * | 1/1999 | Vo-Dinh | 356/301 |
| 5,898,503 A | 4/1999 | Keller et al. | 356/445 |
| 5,912,456 A | 6/1999 | Melendez et al. | 250/216 |
| 5,953,118 A | 9/1999 | O'Rourke et al. | 356/326 |
| 5,955,378 A | 9/1999 | Challener | 436/525 |
| 6,111,248 A * | 8/2000 | Melendez et al. | 250/239 |
| 6,191,847 B1 * | 2/2001 | Melendez et al. | 356/73 |

OTHER PUBLICATIONS

Aldinger, U. et al., "A Comparative Study of Spectral and Angle–Dependent SPR Devices in Biological Applications," *Sensors and Actuators*, B 51 (1998) 298–304.

Cahill, C. et al., "A Surface Plasmon Resonance Sensor Probe Based on Retro–Reflection," *Sensors and Actuators*, B 45 (1997) 161–166.

Cepria, G., "Surface Plasmon Resonance–Based Detection An Alternative to Refractive Index Detection in High–Performance Liquid Chromatography," *Journal of Chromatography*, A 759 (1997) 27–35.

(List continued on next page.)

Primary Examiner—Michael P. Stafira
(74) Attorney, Agent, or Firm—McNair Law Firm, P.A.

(57) ABSTRACT

A surface plasmon resonance ("SPR") probe with a detachable sensor head and system and methods for using the same in various applications is described. The SPR probe couples fiber optic cables directly to an SPR substrate that has a generally planar input surface and a generally curved reflecting surface, such as a substrate formed as a hemisphere. Forming the SPR probe in this manner allows the probe to be miniaturized and operate without the need for high precision, expensive and bulky collimating or focusing optics. Additionally, the curved reflecting surface of the substrate can be coated with one or multiple patches of sensing medium to allow the probe to detect for multiple analytes of interest or to provide multiple readings for comparison and higher precision. Specific applications for the probe are disclosed, including extremely high sensitive relative humidity and dewpoint detection for, e.g., moisture-sensitive environment such as volatile chemical reactions. The SPR probe disclosed operates with a large dynamic range and provides extremely high quality spectra despite being robust enough for field deployment and readily manufacturable.

24 Claims, 6 Drawing Sheets

OTHER PUBLICATIONS

Chinowsky, T. et al., "Optimal Linear Data Analysis for Surface Plasmon Resonance Biosensors," *Sensors and Actuators*, B 54 (1999) 89–97.

Ctyroký, J. et al., "Theory and Modelling of Optical Waveguide Sensors Utilising Surface Plasmon Resonance," *Sensors and Actuators* B 54 (1999) 66–73.

Elkin, J.L. et al., "Integrated Analytical Sensors: The Use of the TISPR–1 as a Biosensor," *Sensors and Actuators*, B 54 (1999) 182–190.

Green, R.J. et al., "Surface Plasmon Resonance for the Real Time in situ Analysis of Protein Adsorption to Polymer Surfaces," *Biomaterials* 18 (1997) 405–413.

Hanning, A. et al., "Enhanced Sensitivity of Wavelength Modulated Surface Plasmon Resonance Devices Using Dispersion from a Dye Solution," *Sensors and Actuators*, B 54 (1999) 25–36.

Homola, J. et al., "Novel Polarization Control Scheme for Spectral Surface Plasmon Resonance Sensors," *Sensors and Actuators*, B51 (1998) 331–339.

Homola, J. et al., "Surface Plasmon Resonance Sensors Based on Diffraction Gratings and Prism Couplers: Sensitivity Comparison," *Sensors and Actuators* B 54 (1999) 16–24.

Homola, J., "On the Sensitivity of Surface Plasmon Sensors with Spectral Interrogation," *Sensors and Actuators* B 41 (1997) 207–211.

Homola, J., "Surface Plasmon Resonance Sensors: Review," *Sensors and Actuators* B 54 (1999) 3–15.

Johnston, K. et al., "Performance Comparison Between High and Low Resolution Spectrophotometers Used in a White Light Surface Plasmon Resonance Sensor," *Sensors and Actuators* B54 (1999) 80–88.

Lyon, L. et al., "Surface Plasmon Resonance of Colloidal Au–Modified Gold Films," *Sensors and Actuators* B 54 (1999) 118–124.

Mar, M. et al., "An Intrinsically Protein–Resistant Surface Plasmon Resonance Biosensor Based Upon a RF–Plasma–Deposited Thin Film," *Sensors and Actuators*, B 54 (1999) 125–131.

Meléndez, J. et al., "Development of a Surface Plasmon Resonance Sensor for Commerical Applications," *Sensors and Actuators*, B 38–39 (1997) 375–379.

Sasaki, S. et al., "Novel Surface Plasmon Resonance Sensor Chip Functionalized with Organic Silica Compounds for Antibody Attachment," *Analytica Chimica Acta*, 368 (1998) 71–76.

Slavik, R. et al., "Minaturization of Fiber Optic Surface Plasmon Resonance Sensor," *Sensors and Actuators*, B 51 (1998) 311–315.

Stemmler, I., et al., "Compact Surface Plasmon Resonance–Transducers with Spectral Readout for Biosensing Application," *Sensors and Actuators*, B 54 (1999) 98–105.

Woodbury, R. et al., "Construction of Biosensors Using a Gold–Binding Polypeptide and Miniature Integrated Surface Plasmon Resonance Sensor," *Biosensors & Bioelectronics*, 13 (1998) 1117–1126.

Wright, J. et al., "The Detection of Phenols in Water Using a Surface Plasmon Resonance System with Specific Receptors," *Sensors and Actuator*, B 51 (1998) 305–310.

* cited by examiner

SURFACE PLASMON RESONANCE SPECTROSCOPY SENSOR AND METHODS FOR USING SAME

POTENTIAL STATEMENT OF PATENT GOVERNMENT RIGHTS

The U.S. government has a paid-up license in this invention and the right in limited circumstances to require the patent owner to license others on reasonable terms as provided for by the terms of Contract No. DE-AC09-96-SR18500 awarded by the Department of Energy.

FIELD OF THE INVENTION

This invention relates to a surface plasmon resonance sensor or probe used in biochemical, chemical, biological or other applications.

BACKGROUND OF THE INVENTION

Surface plasmon resonance ("SPR") is an optical phenomenon caused by the interaction between light or other electromagnetic radiation and several different types of materials, usually comprising a dielectric material and a conductive material arranged in a multi-layer stack of thin films. Technical details describing this optical phenomenon are set forth in various publications, such as one by Schwotzer, et al., titled Fiber Optic. Sensor for Adsorption Studies Using Surface Plasmon Resonance, vol. 2508, Institute of Radio Engineering & Electronics, pp. 324–33, and patents, including U.S. Pat. Nos. 4,997,278 and 5,485,277, each of which documents are incorporated herein by reference.

Basically, however, SPR is an optical phenomenon that occurs when light is shined at a certain angle into a prism that has upon one surface a thin coating comprising one or more conductive or dielectric layers. If the light is shined into the prism at a particular "critical angle," the light may totally internally reflect within the prism so that it does not escape that side of the prism. The critical angle depends upon the characteristics of the prism, the layer(s) or the environment surrounding the entire structure. For instance, an everyday example of total internal reflection occurs when you peer into a clear glass of water. As you change the angle and orientation of the glass relative to your line of sight, at some point you will see the sides of the glass turn opaque or silver. Even though you can normally see through the water in the glass, at the critical angle at which the sides turn silver or opaque, the light is totally internally reflected within the glass and water therein because of the different refractive indices of the water, glass and surrounding air.

Light that totally internally reflects within a coated prism forms an electromagnetic wave that propagates along the conductive (i.e., metal) layer boundary. This wave is known as a surface plasmon. The surface plasmon wave is optically excited at the interface between a conductor or semiconductor, e.g., a metal surface and a dielectric. The optical excitation takes place by an evanescent field, created when light undergoes total internal reflection, for example, off the base of a prism. This evanescent field penetrates the metal and excites a surface plasmon wave where the metal meets the dielectric.

It takes energy to create the surface plasmon. The energy forming the surface plasmon is removed, at a specific frequency or wavelength, from the light that hits the interface between the prism and its coating. Thus, the resulting reflected light beam lacks the removed energy. If you examined the energy in the reflected beam across a spectrum of frequencies or wavelengths, you would see a dip or drop in the energy at a particular "plasmon resonance wavelength," which is the wavelength at which the surface plasmon removes energy from the reflected beam. The plasmon resonance wavelength is determined by a number of factors, including: the thickness, composition and number of the conductive or dielectric layers, as well as the incidence angle of the light upon the substrate, and the interaction between the metal or dielectric layers and the ambient environment.

This surface plasmon resonance ("SPR") phenomenon can be and has been used to create sensors that sense the presence of certain chemical, biological or biochemical agents. For instance, incorporating a particular dielectric or other transducing layer whose permittivity and/or thickness varies in response to chemicals (analytes) of interest results in a sensor whose normal SPR frequency changes with that variation. By analyzing the degree and type of the change, one can determine the presence and/or quantity of a particular analyte of interest. SPR sensors are generally based on bulk optical components (prisms, polarizers, etc.) that yield high quality resonances but which are very difficult to miniaturize into suitable probes for remote sensor applications.

Examples of such SPR sensors are described in U.S. Pat. Nos. 5,485,277 or 4,977,278 or in the Schwotzer, et al. publication cited above. These sensors usually work by shining a collimated light through focusing lenses into a prism or other high refractive index material and then detecting and analyzing the reflected light with a spectrum analyzer. A baseline surface plasmon resonance frequency is found for the particular sensing medium, such as a metallic or other layer of material, coating the prism. The addition of an analyte to the sensing medium changes the SPR frequency. A detector analyzes the reflected light to detect the new SPR frequency. By comparing the new versus baseline frequency, the analyte and/or its quantity can be identified and detected. Such sensors are usually bulky and difficult to keep properly calibrated during their employment.

Indeed, U.S. Pat. No. 4,997,278 to Finland, et al. itself recognizes that one problem with sensors that use a prism or the like is that slight movements of the prism or light source result in changes to the incidence angle, which in turn changes the SPR frequency. That means that the changes to SPR frequency detected by the sensor will be rendered inaccurate or less accurate since variables (e.g., the movement) other than just the presence and amount of analyte will alter the relationship between the baseline SPR frequency and the SPR frequency obtained with the analyte. Prior sensors, including Finland, et al.'s, also use a variety of optics in order to collimate, focus and guide the incident and reflected light beams. These optics contribute to the bulkiness of the probe sensors, rendering them both more expensive to build or maintain and less versatile during use.

Another problem with these conventional SPR probes is that they normally use only one area upon the surface of the probe as the sensing medium. For instance, the Finland, et al. patent applies a sensing layer to the rear, planar surface of an optically transmissive component formed of a slide in contact with a cylindrical lens. Finland, et al., then passes a collimated beam of non-coherent light through the hemispherical portion of the lens so that the light impacts upon the flat surface of the slide upon which the metallic film has been formed. Finland describes the non-coherent light that it shines upon the sensing medium as a fan or cone shaped beam of light. Finland proposes that the advantage of such a fan or cone shaped beam of light is that the range of angles of incidence of the light at the intersection point spans the angle which excites a SPR in the film. Although this allows Finland, et al. to use several beams of light to impact the sensing medium, Finland, et al.'s probes are like prior probes that still use only one portion as a sensing medium and still require monochromatic operation (e.g., use of a particular single wavelength of light) and focusing optics.

SUMMARY OF THE INVENTION

The present invention is an SPR probe that has a substrate with a generally curved reflecting surface. In the present invention, light is input through the substrate to the generally curved reflecting surface where it interacts with one or, optionally, multiple, sensing areas coated with the same or different sensing mediums. By causing the light first to impact against the curved reflecting surface, the light may be reflected from a first impact area to a second, third, etc. impact area. That is because the radius of curvature of the substrate causes the light incident upon the first impact area to reflect to another portion of the substrate with the same incident angle. Thus, for each of the impacts of light on the different portions of the substrate the incident angle remain constant. The number of reflections, and thus the number of light impact and potential sensing areas, can be adjusted by modifying the shape, size and curvature of the curved reflecting surface, as well as the location at which the light enters the substrate. In a preferred embodiment, the curved reflecting surface may be formed as a hemisphere, a shape that is fairly easy to grind to the quality levels required for optical materials.

The invention also involves forming an SPR probe without the need of collimating and/or focusing optics. A probe may be formed by mounting a substrate, such as a substrate with a hemispherical or generally curved surface, on a mandrell or other holding device. Fiber optic lines or light waveguides may be threaded through the mandrell so that an input line provides the incident light that shines through the substrate to impact a generally curved surface coated with a sensing medium. For instance, if a curved or hemispherical substrate is used, the substrate may have a generally planar portion coupled directly to a fiber optic line in order for light to enter the planar portion without distortion and impact the curved reflecting surface. A return fiber optic line may be set within the mandrell at a position that intersects the point at which the curved reflecting surface ultimately reflects the incident light back toward, and through, another generally planar portion of substrate into the return fiber. This structure obviates the need for lenses to focus light upon the substrate. In essence, the substrate itself acts as a lens that focuses the diverging cone of incoming light upon the curved portion of substrate at a stable incident angle. Use of the probe fashioned in this manner, where focusing is acheived by reflection alone, additionally permits the use of white light. Such achromatic operation both eliminates the need for collimating optics and increases the overall range of the available wavelengths for the incident light.

In another embodiment of this invention, the sensing medium coating the curved reflecting surface of the probe may be either a continuous film or an optical diffraction grating. As described in U.S. Pat. Nos. 5,502,560 and 5,610,708 to Anderson, et al., each of which documents are incorporated herein by reference, the reflection spectrum from an optical diffraction grating in contact with sample analytes can be analyzed for intensity and phase modulations that help determine the bulk dielectric properties of the solution or gas in contact with the optical diffraction grating. For instance, the optical diffraction grating can be formed as part of the substrate itself or in the film coating the substrate.

In another embodiment of the invention, the curved reflecting surface of the probe forms a sensor head that may be detachable, facilitating the reuse and reconfiguration of the probe to detect other analytes of interest. In other words, the user can easily swap out a used probe sensor head for an unused or different type of sensor head without having to purchase or replace the entire probe. In one embodiment of this invention, the probe may be an attenuated total reflectance ("ATR") probe, such as the hemispherical ATR probe available from Equitech Int'l Corporation of Aiken, S.C.

Additionally, the present invention can be implemented in an overall system that comprises the probe, with its fiber optic input and detection lines as well as a curved or hemispherical substrate. The probe may be coupled to an input light source for providing light, whether collimated, non-collimated, single or multiple wavelength. The output fiber line of the probe may be coupled to a detector. For instance, a spectrum analyzer may be coupled to the output fiber line in order to analyze the reflected light. A microprocessor-based system may be used automatically to calculate the baseline SPR wavelength and the SPR wavelength following interaction of the sensing medium with the analyte of interest. A display may be coupled to the microprocessor for depicting the baseline and changed SPR wavelengths or frequencies. The microprocessor may incorporate software or couple to a DSP chip for performing filtering or other digital signal processing upon the information the detector provides.

The use of the probe of this invention offers multiple advantages over prior prism or fiber optic based probes. First, the curvature of the probe's reflecting surface and the intimate connection of the fiber to the substrate itself provides a more stable incident angle than a prism substrate than a separate lens and prism substrate configuration. Second, the intimate fiber coupling with the sensor head obviates the need for lenses. Third, the hemisphere or curved sensor portion of the probe may be easily removed, thereby facilitating the reuse and reconfiguration of the probe. Fourth, the probe permits white light, achromatic operation and increases the overall range of the available wavelengths. Another aspect of this invention involves the multiple applications for which it may be deployed. For instance, many current SPR probes are not suitable for field deployment because of their bulk, complexity and fragility. The SPR probe fashioned according to this invention, however, may be used not only for gas phase moisture sensing but also for biological agent detection and commercial gas phase sensing operations in the field.

By way of example, testing and comparison of a sensor fashioned according to this invention against a reference electronic humidity sensor has demonstrated that the SPR sensor of this invention offers substantially better moisture detection performance. Current electronic humidity sensors rely on diffusion through a polymer and take on the order of one or more seconds to respond to humidity changes. The accuracy of these sensors are on the order of one percent relative humidity. The SPR sensor of this invention, however, has a high dynamic range and allows for gas phase kinetic studies to be performed in-situ, thus providing a process-ready sensor that generates better results than currently available sensors. This is particularly critical for certain operations, such as chemical processing that involves volatile or explosive chemicals in which safely tracking relative humidity with a non-electrical sensor is important. By way of example, one embodiment of this invention coats the SPR substrate with a thin metal film that supports the surface plasmon resonance wave, as well as a thin layer of silicon dioxide, $SiO_2$, which acts to sorb water molecules. The process of water adsorption onto and into the sillica layer changes the optical constants and thickness of the material in contact with the metal layer due to the addition of monolayers of water and ocndensed water in the silica pores. The change in optical constants effectively changes the resonance condition and thus the position of the resonance in the optical reflection spectrum. This change in position can be read out using an optical spectrometer and compared against calibrated results to detect the amount of water present. In other words, the sensor can be used to detect relative humidity or dewpoint.

Thus, using the SPR probe of the present invention, faster, more accurate, and more reliable relative humidity data will be available in applications ranging from moisture sensing and drying ovens to air monitoring with a hand-held, portable analyzer.

The present invention accordingly aims to achieve at least one, more or combinations of the following objectives:

- To provide an SPR substrate where input light is incident upon multiple sensing surfaces of the substrate.
- To provide an SPR substrate that has at least a generally curved reflecting surface with one or multiple sensing locations upon the generally curved reflecting surface and with which light entering the substrate interacts.
- To provide an SPR substrate that can be used with non-collimated light.
- To provide an SPR substrate that can be used without one or more lenses for focusing or collimating the entering or reflected light.
- To provide an SPR substrate upon which multiple reactions can take place by modifying the sensing medium at each point of reflection.
- To provide an SPR substrate with a sensing medium formed as a continuous film or with a diffraction grating.
- To provide a sensor probe that has a replaceable sensor head having a substrate with a generally curved reflecting surface.
- To provide a probe that couples to a system for automatically detecting the SPR points of various analytes of interest.
- To provide an SPR probe that may be used in various applications, including applications in which the SPR probe tracts the water vapor concentration in the ambient environment.

Other objects, features and advantages of this invention will become apparent from the rest of this document, including the Figures.

DETAILED DESCRIPTION OF THE DRAWINGS

Overview of the SPR Sensor and Sensing System

Before describing the drawings and embodiments in more detail, several terms are described below in an effort to clarify the terminology used in this document. Additional and fuller understanding of these terms will be clear to persons skilled in this art upon reading this entire document:

"Fiber Optic" means a fiber optic cable or line, or other optical waveguide, that delivers incident light to a portion of the SPR probe or accepts reflected light therefrom.

"Input Surface" means the portion of the SPR sensor head that couples, directly or indirectly, to a fiber optic or other light source for accepting incident light.

"Probe" means a device that delivers incident light to a substrate that acts as an SPR sensor head and removes reflected light therefrom for analysis.

"Reflecting Surface" means the portion of the sensor head against which incident light impacts and is reflected. Depending on the shape and size of the sensor head, as well as the arrangement of the fiber optic or other input light source, there may be multiple reflecting surfaces on any particular sensing head. The reflecting surface often is described as a generally curved surface, which means that it may be curved along one or multiple axes, for instance, forming a cyclindrical, hemispherical or spherical, or even a more complex curved surface.

"Sensing Medium" refers to the layers of conductive or dielectric material that coat at least a portion of the reflecting surface. The sensing medium interacts with or detects the analyte of interest (e.g., water vapor or a particular chemical or biological agent).

"Sensor" or "Sensor Head" refers to that portion of the probe that acts as the SPR substrate and that carries the sensing medium.

Figure 1:
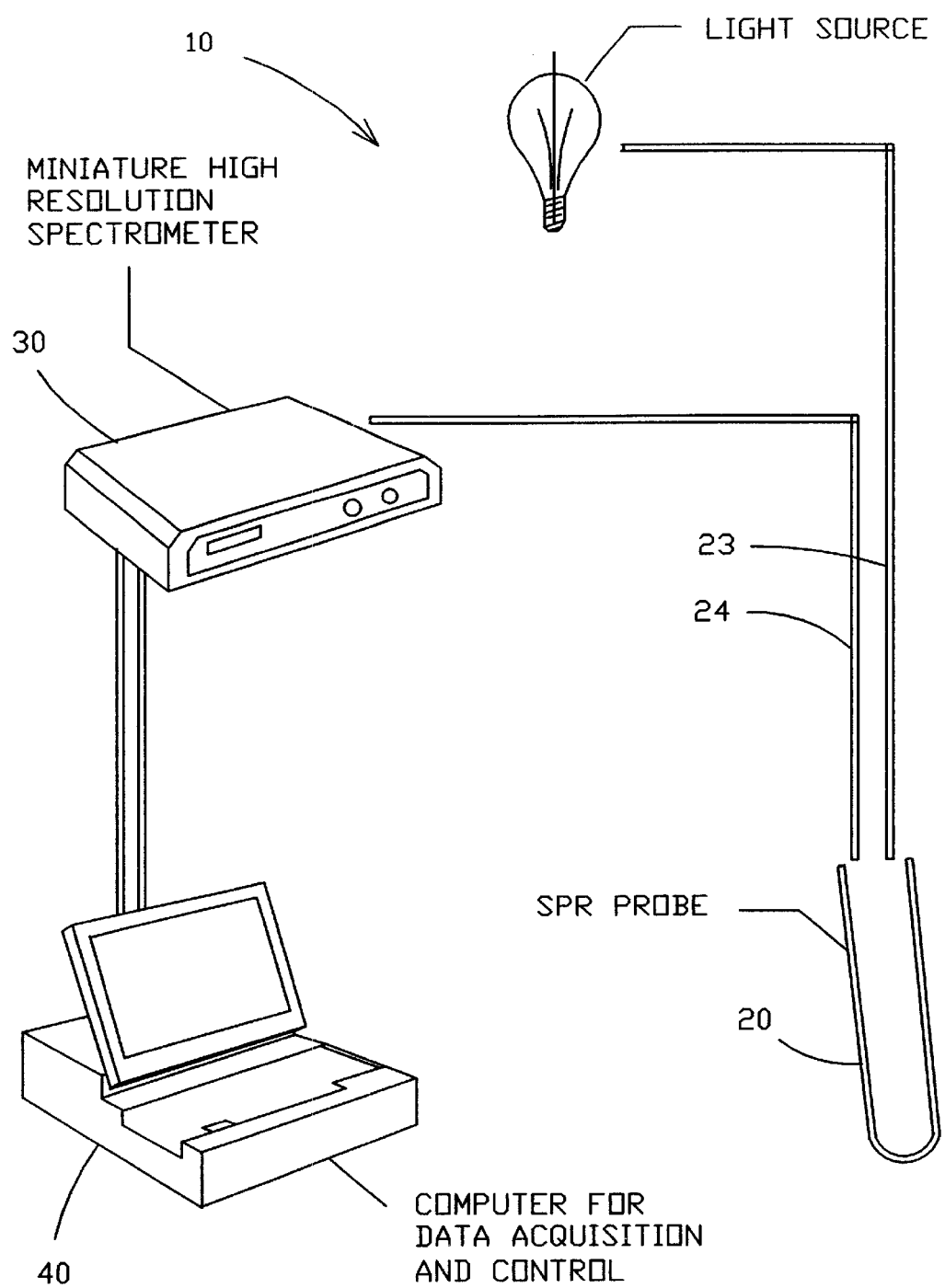
FIG. 1 shows a schematic view of a sensing system using the SPR sensor of the present invention.

FIG. 1 shows an overview of an SPR system 10 that has a probe 20 that couples to a detector 30. Detector 30 may be a spectrum analyzer coupled to a microprocessor 40 and/or a display for outputting information generated by the probe 20, either before or after signal processing on such information by microprocessor 40 or a digital signal processing chipset. Probe 20 has a mandrel (not shown) through which passes lines 23, 24. These lines 23, 24 carry or deliver light to and from a detachable sensor head 50. Mandrel may be formed as a handle if probe 20 is intended for use as a hand held analyzer. Lines 23, 24 may be optical waveguides, such as fiber optic cables, that couple directly to a sensor head 50 attached at the end of the probe 20. Further, probe 20 may be of a monolithic construction with the mandrel molded around lines 23, 24 that increases robustness and fabrication precision.

Figure 2:
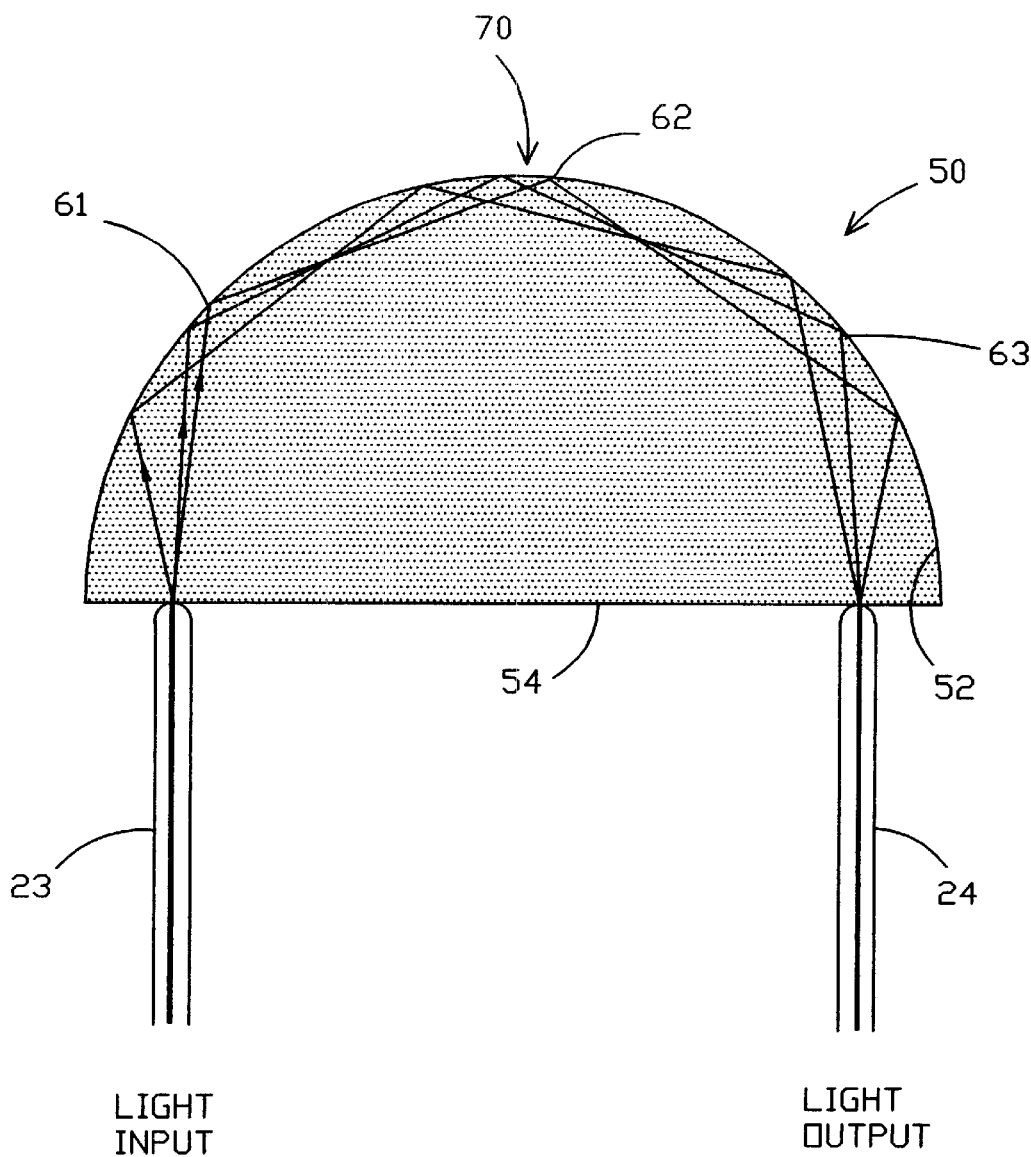
FIG. 2 shows a schematic view of the coupling between an SPR sensor of the present invention and other portions of the probe, including a mandrell and light input/output lines.

FIG. 2 shows the interface between the sensor head 50 and the light input/output lines 23, 24. Sensor head 50 has a generally curved reflecting surface 52, shown in FIG. 2 in the form of a hemisphere, and a generally planar input surface 54. Incident light (Li) input from line 23 passes through input surface 54 and impacts area 61 on the reflecting surface 52. Because of the curvature of the reflecting surface 52 at area 61, the incident light Li is, in turn, totally internally reflected to areas 62 and then 63. The particular embodiment of sensor head 50 shown in FIG. 2 depicts three "bounces" whereby the incident light is bounced from three different parts (61, 62, 63) of the curved reflecting surface 52. Different spacing of the input and output lines 23, 24 yields (a) different numbers of bounces, e.g., 2, 3, 4, 5, 6, 7, etc., bounces and (b) different incident angles. The incident angle is determined by the number of bounces, as demonstrated by the following equation:

$$\theta = \left\{\frac{n-1}{n}\right\} * 90,$$

wherein θ is the incident angle and n is the number of light bounces.

Figure 4A:
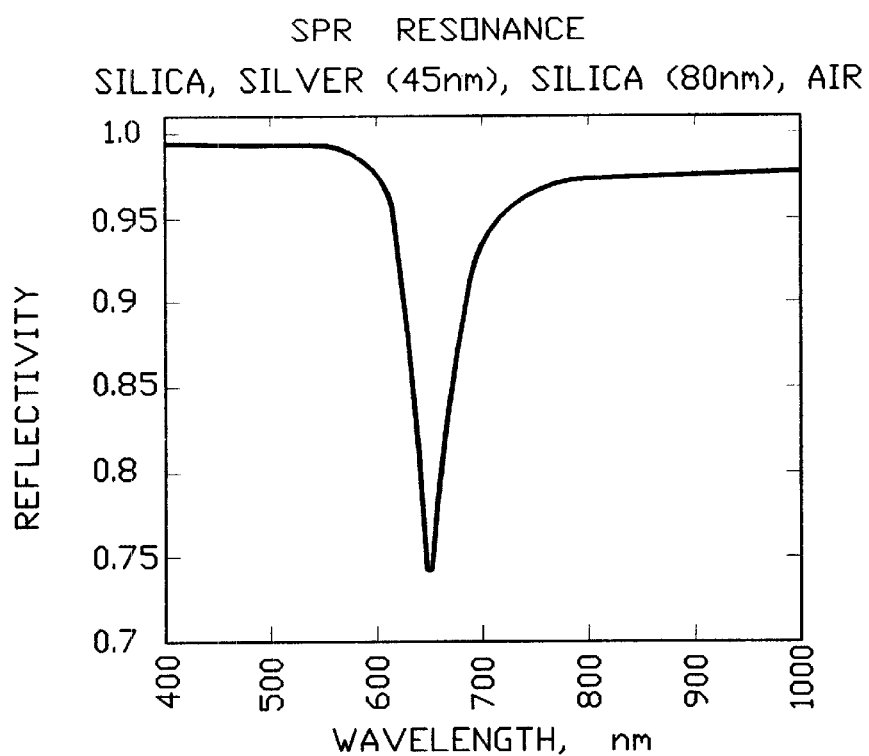
FIGS. 4A and 4B compare the experimental SPR spectrum response of a probe of the present invention with the probe's theoretical SPR spectrum response.
Figure 4B:
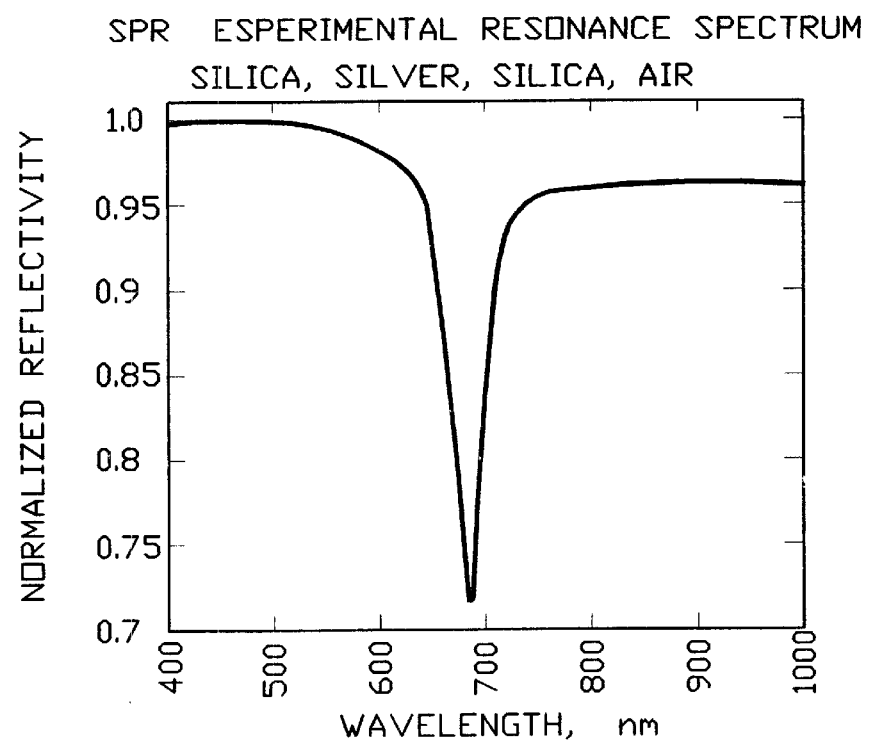

As depicted in FIG. 2, the curvature of the reflecting surface 52 compensates for the divergence of the incident light beam, Li, emitted from an input fiber optic or other light carrying line 23. This preserves the incident angle (60 degrees for a three bounce probe 20) of the beam Li, which in turn yields SPR resonance spectra that approach the theoretical resonance width, as shown in FIG. 4. Such precision results were previously attainable only with sophisticated and expensive optics systems. The high resolution provided by this invention results in a high signal to noise ratio, which allows the probe 20 to be used without polarization optics that otherwise would be needed to remove other light components.

FIG. 2 shows that only area 62 of the reflecting surface 52 is coated with a sensing medium 70. But any, all or combinations of areas 61, 62, 63 may be coated with a sensing medium. Additionally, the number and spacing of areas 61, 62 or 63 may be modified by changing the size, shape or degree of curvature of the sensor head 50 or reflecting surface 52. Changing the position of input line 23 may similarly modify the location of the areas 61, 62 or 63.

In other words, each bounce may activate a surface plasmon resonance wave by applying appropriate coatings, and several sets of input/output lines 23, 24 may be used to generate different regions of SPR activity on sensor head 50. For example, sensor head 50 could have a second set of output/input optical fibers oriented along a different diameter of the bottom, generally planar input surface 54. Different or the same types of sensing mediums 70 can be used on the different impact areas generated by this second set of input/output fibers. As skilled persons can recognize, other sets of input/output lines 23, 24 in different orientations may also be used with sensor head 50, depending upon the surface area available for creating impact areas coated with sensing mediums 70, as well as practical considerations like fabrication constraints. Ultimately, the reflected light Lr is sent into an output line 24, which may lead to a detector 30 or other analyzing device. In a preferred embodiment, the sensing medium 70 may be formed as a tri-layer metal/dielectric structure useful for gas/phase moisture sensing. The layers of metal or dielectric materials may be applied via vacuum sputtering in very thin layers, which may be either continuous or in the form a grating. This thin film sensing medium technology allows fast kinetics with little perturbation of the ambient environment.

Figure 3:
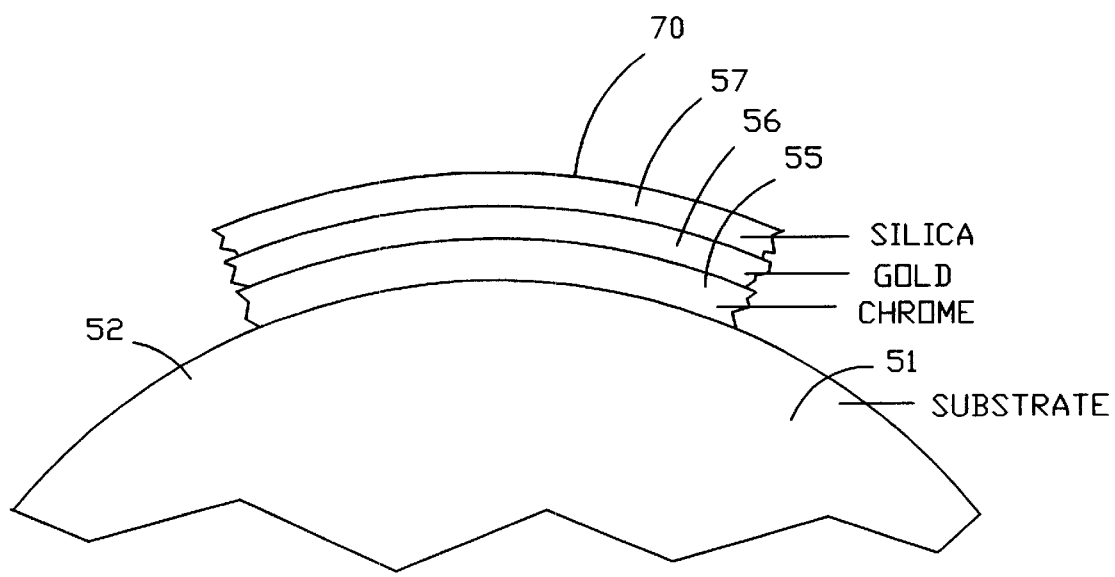
FIG. 3 depicts one embodiment of the invention, a particular sensing medium applied to a probe's sensor head.

FIG. 3 schematically depicts a particular sensing medium 70 applied to the apex of sensor head 50. Sensor head 50 is formed from a substrate 51 and may be detachable. For instance, optical cement or mechanical coupling could be used removably to attach a particular sensor head 50 to the remainder of probe 20. An O-ring can be used to compression couple the sensor head 50 to the probe 20. Such attachment allows easy replacement of sensor heads 50 that have become worn through use or that are inappropriate for sensing a particular analyte of interest. Indeed, it is anticipated that this invention may be offered to the public via (1) a complete sensing system, (2) a probe, (3) replacement sensor heads for a probe or (4) some combination thereof.

As shown in the figures, a significant advantage of one aspect of this invention is that a probe 20 may be formed without the need for collimating or focusing optics. Additionally, the input light source can be a simple, low intensity tungsten-based source (e.g., a light bulb) that needs no stabilization. By measuring the wavelength shift of the reflected light, the present invention may be deployed without a high intensity light source.

Applications

Sensor Fabrication: Two types of trilayer SPR sensor heads were fabricated via a three step deposition process. The first type used silver as the conductive layer; the second type used gold as the conductive layer. FIG. 3 schematically shows the sensor head 50 configuration. First, hemispheres fashioned of an optically appropriate material (e.g., silica, sapphire, cubic zirconia, etc.) were cleaned and dried in a dry Ar jet and placed into a vacuum coating system which utilizes two planar magnetron sputter sources with either direct current or radio frequency excitation of an Argon plasma. This sputtering technique is a standard technique for depositing thin, reproducible films on various substrates. The curved surface 52 of the hemisphere was coated with a thin (20 angstrom) layer of chromium followed by a layer of gold or silver having final thickness between 100 and 1000 angstroms. The chromium layer served to improve adhesion between the gold or silver layer and the substrate material. The thickness of the metal layer controls the quality and depth of the measured SPR resonance. After deposition of the metal layer, a final layer of dielectric material, in this case silica, was applied using the RF supplied sputter source. The layer thickness may be varied between 100 and 1000 angstroms, depending upon the dielectric material chosen and the optical requirements set forth by the detection system. All thicknesses are measured in-situ by a quartz crystal microbalance, or ex-situ using a thin film measurement technique such as ellipsometry or depth profiling.

The optical system was assembled and used to measure the SPR spectrum from the first hemisphere probe, made of gold and silica, in ambient and dry air. The initial spectrum was obtained and compared with the spectrum generated by modeling the optical system using Fresnel reflection equations and solving for intensity. In this way the experimental spectrum may be compared with the expected, or theoretical, spectrum. This comparison is given in FIGS. 4A and 4B. The key point to be made via comparison of these spectra is that the experimental spectrum matches closely the theoretical spectrum, both in resonance depth and width. This indicates that the incident angle is held constant at 60 degrees for this geometry, and further validates the structure. In short, this is the first demonstration of a simple, single element probe geometry which yields an SPR spectrum that approaches the theoretical limit of resolution and width, once only achievable in expensive, bulky laboratory optical systems.

According to these results, the hemispherically shaped probe 20 and sensor head 50 perform close to the theoretical resolution limit for prior SPR laboratory systems that require highly-collimated input light. These very high resolution spectra obtained with the probe 20 enables sensitive detection of analytes of interest and also demonstrates the viability of this probe 20 construction for either gas or liquid phase sensing. Yet the probe 20 of this invention, despite containing no focusing or polarization optics, yielded high-quality, low noise SPR spectra from its compact, fiber-coupled sensor head 50.

Skilled persons will understand that various different configurations of sensing medium 70 may be used upon SPR sensor heads. For instance, the thickness and composition of the metal or dielectric layers may be varied depending on the particular application for the sensor head 50. Thus, if the sensor head 50 will be used to interact with chemical or biological samples, the dielectric or metallic layers may be varied, depending on the sample of interest. Once those layers interact with the chemical or biological material of interest, knowing the expected, baseline resonance of the initial layers allows detection of the concentration of the chemical or biological species in the sample.

The overall response of the sensor head 50 is sensitive to manufacturing parameters, such as sputtering parameters, porosity, and film pretreatment. Another factor that will influence the particular design of sensor head 50 is the desire to vary the angle of incidence against the curved reflecting surface based on the varying refractive indices that the sensor head 50 will encounter in use. In other words, one must "tune" the sensor to account for the dynamic range of incident angles and wavelengths that differences in refractive indices cause. Thus, for a given material and analyte of interest, skilled persons will recognize that sensor head 50 fabrication must be modified, e.g., by changing the material forming the sensor head 50, the sensing medium 70, or both.

Precision moisture detection applications: The sensor head 50, in either the gold/silica or the silver/silica configuration, proved to be very sensitive to changes in the relative humidity around the head. The response time for instantaneous changes in humidity is on the order of 0.1 seconds ("s") with little initial hysteresis. The silver/silica sensor head 50 proved unsuitable for long term SPR sensing in air as the moisture in the atmosphere oxidizes the silver surface and causes the SPR signal to degrade. Therefore, the gold/silica probe 20 format is the preferred embodiment as gold resists corrosion.

The sensor head 50, after initial characterization and qualitative evaluation, was subjected to various controlled humidity environments in order to test the sensitivity of the SPR sensor to adsorbed moisture. The nominal sensor head configuration for the experiments described below included a thin chromium adhesion layer, a 450 angstrom layer of gold, and a 750–800 angstrom layer of silica.

Figure 5A:
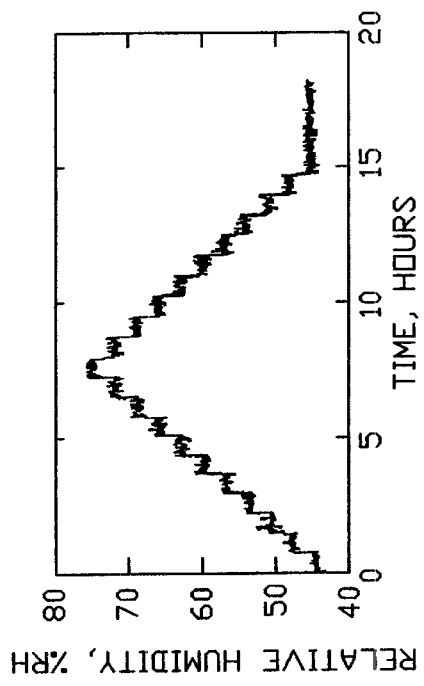
FIGS. 5A through 5D graph the results of a probe fashioned according to this invention used in an application that involves sensing relative humidity.
Figure 5C:
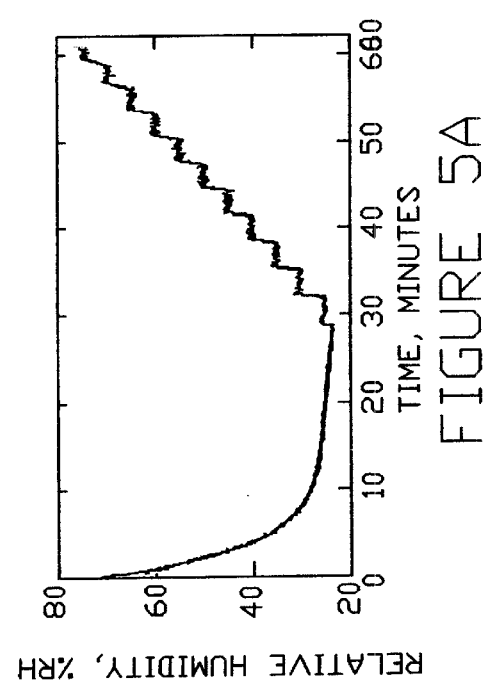
Figure 5B:
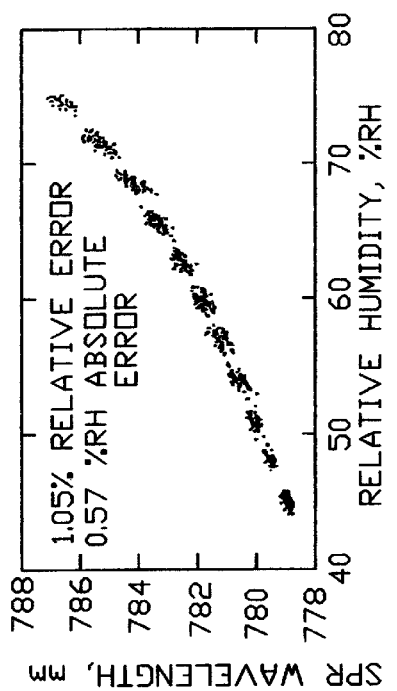
Figure 5D:
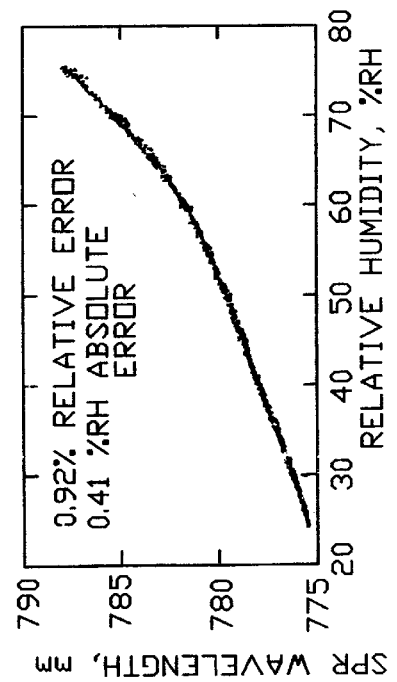

First, the sensor was placed in a large (1 cubic foot) chamber with a recycling pump, drying tube, and ultrasonic humidity generator. This system was capable of generating humidities in the range of 10% to 100% relative humidity. The chamber humidity was stepped up and down via computer control and the SPR spectrum recorded as a function of time and humidity. FIGS. 5A through 5B compare the resonance wavelength obtained from the gold/silica sensor head 50 used with probe 20 with baseline humidity values obtained from a capacitive RH sensor with an accuracy of 1% for short-term, controlled humidity changes. FIGS. 5C and 5D show the long-term (18 hours) response of the same probe 20. These graphs demonstrate the responsiveness of the SPR probe 20, For instance, experimental data showed that the gold/silica sensor head 50 responded with a sensitivity of 0.025% relative humidity. This data indicates that the sensor head 50 and probe 20 operate reproducibly over a wide range of what would be considered atmospheric humidities.

The sensor head 50 was also tested for its response to very low (parts per million) levels of water in dry gas lines. In order to accomplish this, a second characterization system was assembled which allowed for very low humidities to be generated and measured to a high degree of accuracy using a NIST-traceable reference method. The data generated in this experiment were in units of dewpoint, degrees Celsius, which could be converted to parts per million via a standard atmospheric calculation relating pressure, measured dewpoint, and temperature, to concentration of water in the vapor phase. A dewpoint generator and a reference chilled-mirror dewpoint hygrometer were used to test the response of a probe 20 over a several day trial period over a wide range of dewpoints.

Figure 6:
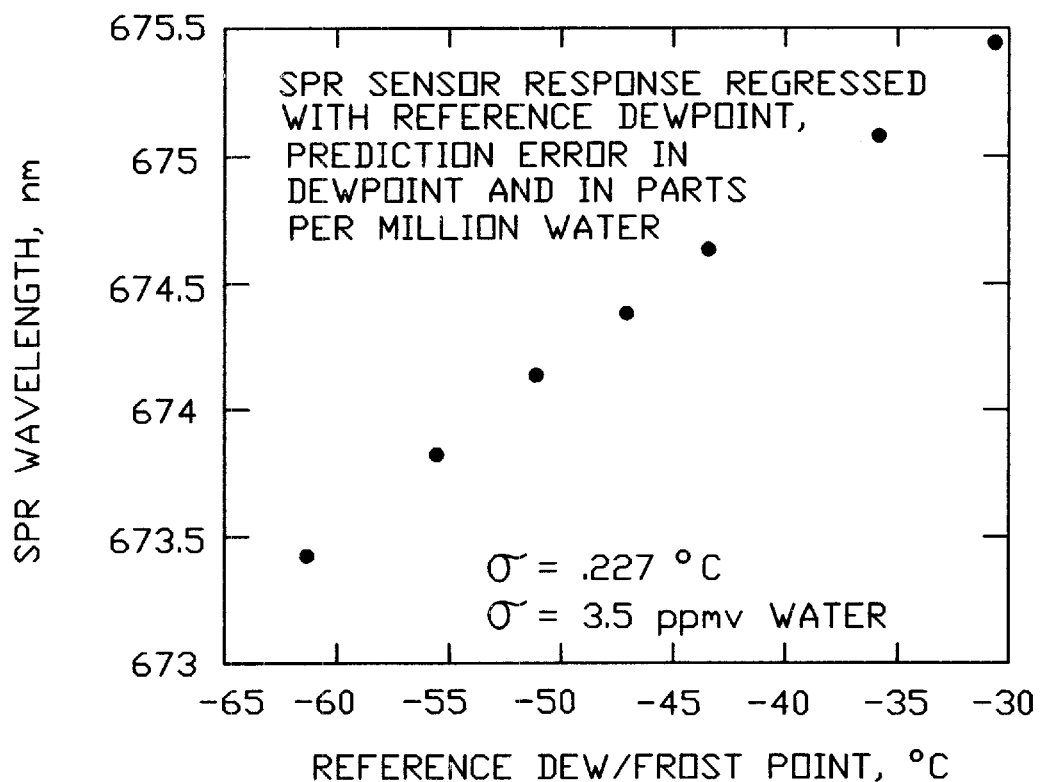
FIG. 6 graphs the SPR resonance position response to changing levels of moisture in nitrogen.

FIG. 6 shows a particular probe 20's SPR resonance position variation in reaction to changes in levels of moisture in nitrogen. The SPR response of a probe 20 was regressed with the reference dewpoint and a fit error generated. The results indicate that the SPR sensor head 50 could predict dewpoint and/or water concentration to very high accuracy and precision given the linear fit. In other words, the SPR sensor head 50 responds linearly with dewpoint changes and is capable of detecting very low levels of moisture, on the order of parts per million. Additional experimental data has demonstrated that a probe 20 of this invention is sensitive to a dewpoint of 0.75 parts per million (750 parts per billion), or capable of detecting relative humidity changes on the order of 0.005%. Indeed, experiments resulted in probe 20 continuing to detect dewpoint changes after the reference sensor had bottomed out.

Additionally, the probe 20 fashioned according to this invention has a very large dynamic range from less than one part per million to greater than 20,000 parts per million by weight. This upper range is calculated based on the previous sensitivity to high relative humidity values. The saturation concentration, or 100% relative humidity, of water at ambient conditions is approximately 20,000 parts per million by weight. Therefore, the demonstrated low humidity and high humidity sensitivity indicate that the sensor has a very wide dynamic range for moisture detection. In short, performance of the probe 20 in a moisture sensing application greatly exceeds performance on conventional optically-based sensors.

Stabilization of the sensor head 50 for long-term monitoring likely can be improved by minimizing stress in the silica film. That may be done by employing different deposition parameters. Additional ways to minimize hysteresis or long-term sensor drift may include annealing in the structure after deposition to stabilize the mechanical and optical properties of the film. An in situ annealing heater stage may be operated in a vacuum chamber in order to accomplish this step. Additionally, sputtering at higher pressures should yield more porous films, which would be less susceptible to compressive stresses induced by water adsorption. Annealing may also reduce the intrinsic stress in the lattice, thus reducing the number of strained silicon oxide bonds that are more active than relaxed bonds. Also, there is the option of aging the sensor and cycling the relative humidity until the response has stabilized.

The sensor head 50 and probe 20 of the present invention provides a sensitive, selective and intrinsically safe moisture sensitive for hazardous environments. For instance, prior sensors do not allow the precision and response of this invention with the safety provided since this invention offers no electrical spark hazard. Nor, if properly formulated and applied, will the sensor head 50, or the sensing medium 70 thereon, degrade in the presence of chemical or radiation hazards.

The foregoing is provided for purposes of illustrating, explaining and describing several embodiments of the present invention. Modifications and adaptations to these embodiments will be apparent to those of ordinary skill in the art and may be made without departing from the scope or spirit of the invention and the following claims. For instance, the exact shape of the probe's reflecting surface may be modified to a multifaceted surface rather than simply a curved surface. Also, the embodiments described in this document in no way limit the scope of the below claims as persons skilled in this art recognize that the present invention can be easily modified for use with other devices and systems.

What is claimed is:

1. A surface plasmon resonance probe comprising a substrate directly coupled to an input line that delivers, without a collimating or focusing lens, incident light into the substrate, a portion of which reflects the incident light out of the substrate through a directly coupled output line spaced apart from the input line after the incident light interacts with at least one sensing medium coupled to the substrate.

2. A probe according to claim 1 in which the portion of substrate that reflects the incident light comprises a generally curved reflecting surface, which has at least a portion thereof coated with a sensing medium.

3. A probe according to claim 2 in which the portion of substrate that reflects the incident light comprises a generally hemispherical reflecting surface that acts to compensate for divergence of the light incident on the reflecting surface.

4. A probe according to claim 3 further comprising a handle surrounding at least the input line and the output line that accepts light reflected from the substrate and sensing medium.

5. A probe according to claim 1 in which the incident light is non-collimated and the sensing medium comprises at least one conductive layer and at least one layer comprising either a bulk medium or a thin film of dielectric material.

6. A replaceable sensor adapted for use in a surface plasmon resonance probe having an input light source, in which the sensor comprises:
    a curved reflecting surface against which non-collimated incident light from the input light source is reflected;
    at least one area coated with at least one sensing medium, whereby incident light interacts with the sensing medium to generate a surface plasmon; and
    a surface adapted to couple to the probe.

7. The sensor according to claim 6 in which the substrate is adapted to support multiple sensing mediums, at least one of which is formed either as an optical diffraction grating or as a continuous film.

8. The sensor according to claim 7 in which the geometry of the substrate causes incident light to interact with each of the multiple sensing mediums.

9. The sensor according to claim 6 in which the curved reflecting surface forms a hemispherical shape.

10. A method for using an SPR probe with a generally curved reflecting surface having a sensing medium on at least a portion thereof, which method comprises applying electromagnetic radiation comprising non-collimated light to the generally curved reflecting surface in order to cause the sensing medium to generate a surface plasmon.

11. A method according to claim 10 further comprising the step of detecting light reflected from the sensing medium in order to sense an analyte of interest.

12. A method according to claim 11 wherein the non-collimated light is comprised of a continuum of frequencies.

13. A method according to claim 10 wherein a second sensing medium is applied to a second portion of the generally curved reflecting surface.

14. A method according to claim 10 wherein the applying step comprises the steps of coupling an input source directly to a portion of the probe in order to deliver non-collimated light.

15. A method for using an SPR sensor comprising a generally curved reflecting surface and at least one surface plasmon-generating sensing region thereon, which method comprises:
    placing the sensor in the vicinity of a material comprising at least one target analyte;
    applying non-collimated electromagnetic radiation to one or more of the plasmon-generating sensing regions in order to cause the sensing region or sensing regions to generate one or more surface plasmons; and
    comparing the plasmons generated in the presence of the target analyte to those generated in the absence of the target analyte.

16. A surface plasmon resonance ("SPR") probe comprising a substrate coated with a sensing medium and coupled directly to an input that delivers incident light to the substrate.

17. The probe of claim 16 wherein the probe is adapted for use in moisture detection over a range of about less than one part per million moisture to about 20,000 parts per million moisture.

18. The probe of claim 16 in which the substrate comprises a generally curved reflecting surface that acts to compensate for divergence of the light incident on the reflecting surface and the input comprises a fiber optic.

19. The probe of claim 18 further comprising an output fiber optic for delivering reflected light to a spectrograph and a handle surrounding at least the input and output fiber optics that accepts light reflected from the substrate and sensing medium.

20. A system for detecting analytes of interest, the system comprising:
    a surface plasmon resonance ("SPR") probe adapted for operating without a lens for focusing incident light; and
    a light source and a detector associated with the probe, wherein the light source provides the incident light and the detector detects the SPR resonances of at least one analyte of interest.

21. A system according to claim 20 further comprising a microcomputer for comparing the detected SPR resonances with baseline SPR resonances in order to identify the analyte of interest.

22. A system according to claim in which the probe comprises a replaceable sensor head formed of a substrate and at least a first sensing medium coupled thereto.

23. A system according to claim 22 in which the replaceable sensor head has multiple sensing mediums to interact with incident light, at least one of such sensing mediums being formed as an optical diffraction grating.

24. A system according to claim 23 in which the substrate has a generally curved reflecting surface holding the sensing medium against which the incident light reflects in order to form a surface plasmon wave at the interface between the generally curved reflecting surface and the first sensing medium.

* * * * *

UNITED STATES PATENT AND TRADEMARK OFFICE
CERTIFICATE OF CORRECTION

PATENT NO.    : 6,466,323 B1
DATED         : October 15, 2002
INVENTOR(S)   : Brian Benjamin Anderson et al.

It is certified that error appears in the above-identified patent and that said Letters Patent is hereby corrected as shown below:

Drawings,
Figures 5B and 5D, after "SPR WAVELENGTH," change "mm" to read -- nm --.

Column 2,
Line 27, please change "4,977,278" to read -- 4,997,278 --.

Signed and Sealed this

Twenty-fourth Day of June, 2003

JAMES E. ROGAN
*Director of the United States Patent and Trademark Office*